United States Patent [19]

Delaire

[11] Patent Number: 5,350,298
[45] Date of Patent: Sep. 27, 1994

[54] METHOD AND CANAL INSTRUMENT FOR FILLING AND/OR COATING THE WALLS OF AN ENDODONTIC CANAL

[75] Inventor: Jacques Delaire, Besancon, France

[73] Assignee: Micro Mega SA, Besancon, France

[21] Appl. No.: 989,111

[22] Filed: Dec. 11, 1992

[51] Int. Cl.$^5$ .............................................. A61G 5/02
[52] U.S. Cl. ................................... 433/81; 433/102; 433/224
[58] Field of Search .................. 433/81, 102, 164, 224

[56] References Cited

U.S. PATENT DOCUMENTS

| | | | |
|---|---|---|---|
| 1,969,808 | 8/1934 | Lentulo | 433/164 |
| 4,229,168 | 10/1980 | Scholz, Jr. | 433/124 |
| 4,260,379 | 4/1981 | Groves et al. | 433/102 |
| 4,353,698 | 10/1982 | McSpadden | 433/164 |
| 4,871,312 | 10/1989 | Heath | 433/81 X |
| 4,971,556 | 10/1990 | Ritano | 433/102 |
| 5,098,298 | 3/1992 | Johnson | 433/81 X |
| 5,106,298 | 4/1992 | Heath et al. | 433/102 |

FOREIGN PATENT DOCUMENTS

| | | |
|---|---|---|
| 0059656 | 9/1982 | European Pat. Off. . |
| 845093 | 7/1952 | Fed. Rep. of Germany ...... 433/102 |
| 3532548 | 3/1986 | Fed. Rep. of Germany ...... 433/102 |

*Primary Examiner*—Gene Mancene
*Assistant Examiner*—Nicholas D. Lucchesi
*Attorney, Agent, or Firm*—Weiser & Associates

[57] ABSTRACT

A canal instrument intended to be mounted on the head of a vibrating handpiece and allowing the application in the dental canal of filling paste by applying successive layers in order either to produce a complete filling or to produce a thin layer on the walls of the canal with a view toward lubrication or blocking-out of the spaces which can be left free by condensed gutta-percha points, including a handle (1) of known type for its fastening to the vibrating handpiece and a blade (2) provided over a part of its length, starting from its distal end, with one or more helicoid grooves whose edges (3) are rounded in order to prevent any cutting effect, and therefore reaming the root canal.

19 Claims, 2 Drawing Sheets

METHOD AND CANAL INSTRUMENT FOR FILLING AND/OR COATING THE WALLS OF AN ENDODONTIC CANAL

The present invention relates to the field of endodontic instrumentation and more particularly to a device for applying canal filling pastes. Its subject is also a method for canal filling using the said instrument.

Such canal filling may be produced mainly with gutta-percha points or with filling pastes, or alternatively with instruments like those described in U.S. Pat. No. 4,758,156 of Willie B. JOHNSON.

In the case of gutta-percha points, the vertical or lateral condensation is obtained from points with circular cross-section which fill a canal of non-circular geometry. There is therefore always the risk that spaces remain between the various points inserted into the canal.

The obturation pastes are generally introduced into the canal by instruments called paste carriers, like those described for example in the standard ISO 3630. These paste carriers are generally mounted on contra-angle handpieces, which constrains the practitioner to use two handpieces for the endodontic treatment. These paste carriers furthermore have the principal effect of pushing the paste to the bottom of the canal without producing any projection against the walls of the canal, whence the risk of poor sealing.

As regards the instruments described by JOHNSON in U.S. Pat. No. 4,758,156, without prejudging their effectiveness, it is certain that in order to facilitate their introduction, it is necessary to provide a certain lubrication in order to facilitate their penetration into the canal, which lubrication must be made by applying a thin layer of filling paste.

The object of the present invention is to provide an instrument which overcomes the aforementioned drawbacks.

More precisely, the invention provides a canal instrument intended to be mounted on the head of a vibrating handpiece and allowing the application in the dental canal of filling paste by applying successive layers in order either to produce a complete filling or to produce a thin layer on the walls of the canal with a view toward lubrication or blocking-out of the spaces which can be left free by the condensed gutta-percha points. The canal instrument is composed of a handle of known type for its fastening to the vibrating handpiece and of a blade and is characterised in that the blade is provided, over part of its length starting from its distal end, with one or more helicoid grooves whose edges are rounded in order to prevent any cutting effect, and therefore reaming of the root canal. Another important characteristic of the invention is that the diametral and length dimensions as well as the characteristic materials are chosen together such that during the vibration imparted by the handpiece to the instrument, the latter has no vibrational node along its length other than that represented by its point of fastening to the handpiece such that there can be no accumulation of paste at such a vibrational node, which paste would not then be projected against the walls of the canal.

A third characteristic is that the instrument will preferably be produced in a conical shape so that it matches the canal anatomy better, and that there are series of instruments of different conicity, each series having a constant tip diameter.

The helicoid groove is chosen to be right-handed or left-handed such that the vibration imparted by the handpiece is converted into a left-handed or right-handed circular motion so that the longitudinal motion of the paste is toward the apex of the canal.

The invention will be better understood with the aid of the following description which will be given, by way of non-limiting example, of a preferred embodiment with reference to the attached drawings in which:

FIG. 1 represents the instrument according to the invention comprising a handle (1) and a blade (2) fixed to the handle in a known manner.

The blade (2) is cut over a large part of its length so as to have at least one helicoid groove and so that the geometrical envelope of the cut part is conical, the point diameter being situated at the tip of the instrument, that is to say at its distal end.

Figure 2:
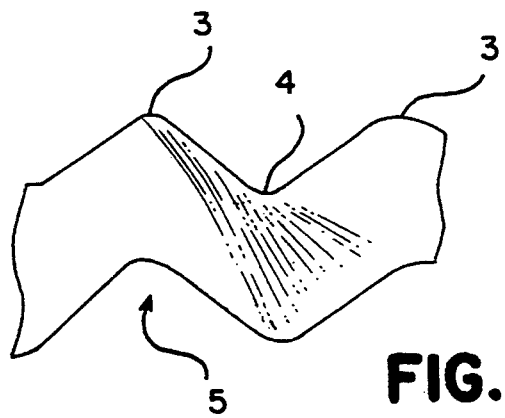
FIG. 2 represents an enlarged view of portions of the blade of the instrument in FIG. 1.

As indicated in FIG. 2, the helicoid groove is such that the edges (3) generated during its production are rounded in order to prevent any cutting phenomenon. Furthermore, the bottom of the groove is also of rounded shape (4) in order to avoid accumulation of paste in a corner which thus ensures correct ejection of the paste.

When the instrument is loaded with paste, the latter will fill the space in the groove (5).

Figure 3:
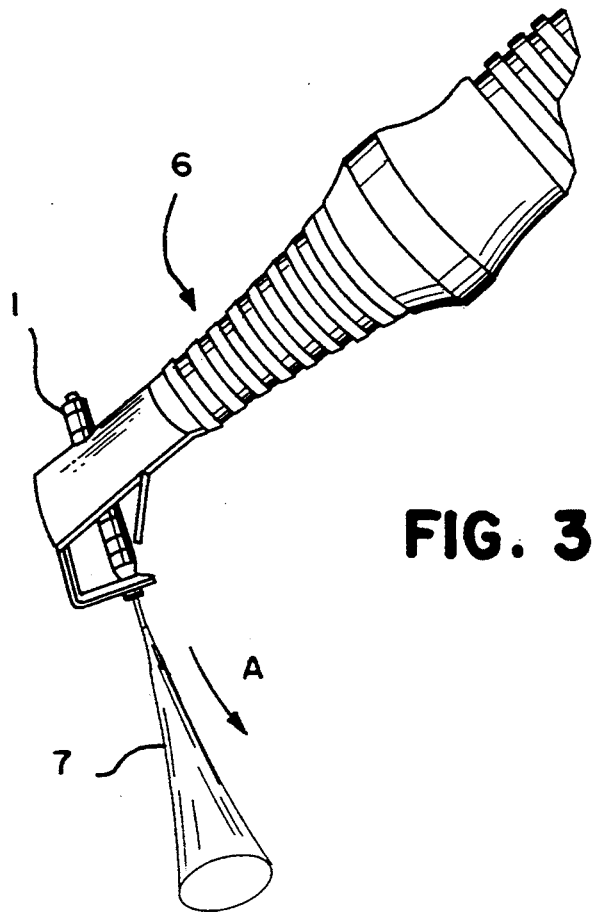
FIG. 3 represents the movement envelope of the instrument according to the invention, the instrument being mounted on a vibrating handpiece, FIGS. 4, 5 and 6 diagrammatically represent the results of employing the device of the invention on a canal filling.

FIG. 3 represents the instrument according to the invention mounted on a vibrating handpiece (6) via its handle (1). The envelope (7) of the movement of the blade of the instrument (excited in vibration) is seen in this figure. With the instrument loaded with paste, the vibrational movement will cause a displacement of the paste in the direction (A) until, progressively, the components of force applied to the paste in the direction perpendicular to the axis of the instrument cause ejection of the paste along these perpendicular directions. It is thus understood that a covering of the walls of the canal will be obtained in the canal by a "pargeting" effect.

Figure 4:
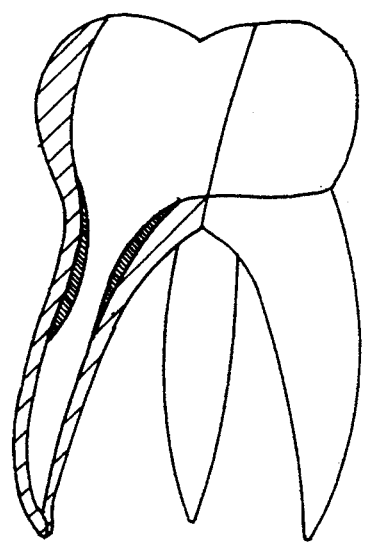
Figure 5:
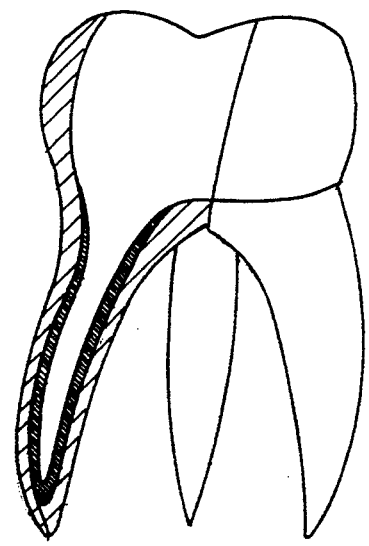
Figure 6:
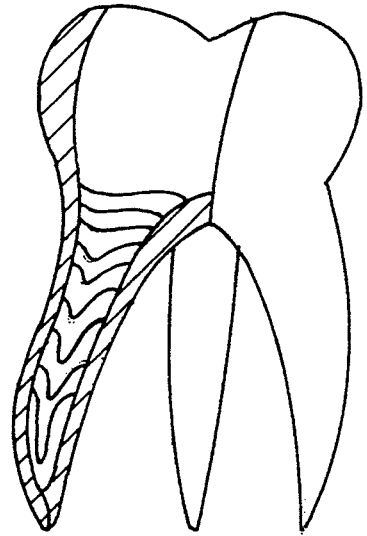

It is thus possible to obtain equally well:

as indicated in FIG. 4, a partial coating at the entry of the canal which will be used as lubricant for the gutta-percha point or for the instruments according to the aforementioned United States patent, or a complete coating represented in FIG. 5 which will allow the filling obtained to be completed using gutta-percha points, or alternatively, by successive layers, a complete filling of the canal as indicated in FIG. 6.

In order to improve the effectiveness during projection, the groove pitch decreases progressively toward the tip of the instrument, which has the effect of reducing the space left by the helicoid groove thus facilitating the ejection of the paste.

It is possible to improve the result by progressively reducing the depth of the groove toward the tip.

Figure 1:
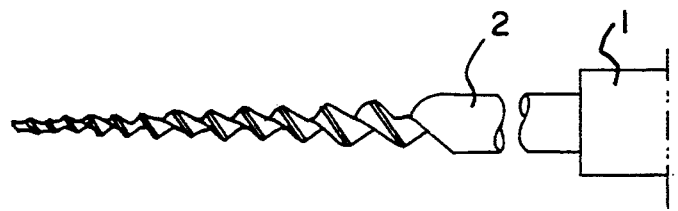
FIG. 1 represents an elevation of the instrument according to the invention.

Finally, as represented in FIG. 1, it is possible to judiciously combine the above two ideas.

I claim:

1. A canal instrument adapted for mounting to a head of a vibrating handpiece, for applying a filling paste in a dental canal by applying layers to either produce a complete filling or to produce a thin layer on walls of the canal, comprising a handle portion for attachment to the handpiece, and a blade portion including a body and at least one helicoid groove formed in the body and extending from a distal end of the body and along at least portions of the body, wherein the helicoid groove has rounded outer edges to prevent any cutting effect, and reaming of the canal.

2. The canal instrument of claim 1 wherein the body is a solid body.

3. The canal instrument of claim 2 wherein the helicoid groove has rounded base portions separating adjacent outer edges of the helicoid groove.

4. The canal instrument of claim 3 wherein the helicoid groove has a pitch that decreases toward the distal end of the body.

5. The canal instrument of claim 4 wherein the helicoid groove has a depth that decreases toward the distal end of the body.

6. The canal instrument of claim 1 wherein the body has a conical shape.

7. The canal instrument of claim 6 wherein the helicoid groove defines an envelope that is conical, and wherein the conical envelope narrows toward the distal end of the body.

8. The canal instrument of claim 1 wherein the body has a diameter and a length and is formed of a material selected so that any vibrational node formed along the body responsive to vibration of the body by the handpiece is located only where the handle portion is attached to the handpiece.

9. The canal instrument of claim 1 wherein the helicoid groove is shaped so that vibration of the blade portion longitudinally moves the past toward the distal end of the body.

10. The canal instrument of claim 9 wherein the helicoid groove is left-handed, so that vibration of the blade portion produces a left-handed circular movement of the body.

11. The canal instrument of claim 9 wherein the helicoid groove is right-handed, so that vibration of the blade portion produces a right-handed circular movement of the body.

12. A plurality of canal instruments according to claim 1, wherein the canal instruments each have a different conicity, and a constant diameter at the distal ends thereof.

13. A method for filling a canal with an instrument mounted to a head of a vibrating handpiece, the instrument including a handle portion for attachment to the handpiece, and a blade portion including a body and at least one helicoid groove formed in the body and extending from a distal end of the body and along at least portions of the body, wherein the helicoid groove has rounded outer edges to prevent any cutting effect, and reaming of the canal, and the method comprises the steps of:

applying a filling paste to the helicoid groove of the instrument;

vibrating the instrument within the handpiece; and applying a coating of the filling paste to portions of the canal.

14. The method of claim 13 which further includes the step of applying a partial coating of the filling paste to entry portions of the canal, for lubricating the entry portions of the canal to receive a gutta-percha point or a canal instrument.

15. The method of claim 13 which further includes the step of applying a complete coating of the filling paste to the canal, for completing the filling with gutta-percha points.

16. The method of claim 13 which further includes the step of applying successive layers of the filling paste to the canal, for completing the filling of the canal.

17. The method of claim 13 wherein the vibrating of the instrument longitudinally moves the filling paste toward the distal end of the body.

18. The method of claim 17 wherein the helicoid groove is left-handed, so that vibration of the blade portion produces a left-handed circular movement of the body.

19. The method of claim 17 wherein the helicoid groove is right-handed, so that vibration of the blade portion produces a right-handed circular movement of the body.

* * * * *